(12) United States Patent
Matsunaga et al.

(10) Patent No.: US 7,524,977 B2
(45) Date of Patent: Apr. 28, 2009

(54) PROCESS FOR PRODUCING FLUOROALKANESULFONAMIDE DERIVATIVES

(75) Inventors: Kei Matsunaga, Saitama (JP); Takeo Komata, Saitama (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 11/878,593

(22) Filed: Jul. 25, 2007

(65) Prior Publication Data

US 2008/0058538 A1    Mar. 6, 2008

(30) Foreign Application Priority Data

Jul. 26, 2006  (JP) .............................. 2006-204019
Aug. 25, 2006  (JP) .............................. 2006-229847
Jun. 29, 2007  (JP) .............................. 2007-173217

(51) Int. Cl.
C07D 307/00    (2006.01)
C07C 315/00    (2006.01)
C07C 317/00    (2006.01)

(52) U.S. Cl. .................. 549/463; 549/467; 568/30; 568/31

(58) Field of Classification Search ........... 549/463, 549/467; 568/30, 31
See application file for complete search history.

(56) References Cited

U.S. PATENT DOCUMENTS 5,514,493 A    5/1996   Waddell et al.
5,723,664 A    3/1998   Sakaguchi et al.
5,874,616 A    2/1999   Howells et al.

FOREIGN PATENT DOCUMENTS

JP    8-81436 A     3/1996
JP    11-209338 A   8/1999
WO    WO 97/23448   7/1997

OTHER PUBLICATIONS

Zhurnal OrganicheskolKhlmil (Russia), (1995), 31(3), p. 357-364.
"Fluorinated Sulphonic Acids. Part I. Perfluoro-methane-, -octane-, and -decane-sulphonic Acids and their Simple Derivatives," Journal of Chemical Society, vol. 6 (5), p. 2574-2578 (published in 1957).

*Primary Examiner*—Janet L. Andres
*Assistant Examiner*—David Gallis
(74) *Attorney, Agent, or Firm*—Crowell & Moring LLP

(57) ABSTRACT

There is provided a process for producing a fluoroalkanesulfonamide derivative represented by the formula [3], $$R^2-NH-SO_2-R_f-R^1 \quad [3]$$

including reacting a fluoroalkanesulfonic anhydride represented by the formula [1], with an organic primary amine represented by the formula [2], in the presence of water and in the presence of a base selected from the group consisting of (a) a hydroxide of an alkali metal or alkaline-earth metal or (b) a basic salt containing an alkali metal or alkaline-earth metal.

13 Claims, No Drawings

PROCESS FOR PRODUCING FLUOROALKANESULFONAMIDE DERIVATIVES

TECHNICAL FIELD

The present invention relates to a process for producing fluoroalkanesulfonamide derivatives, which are useful compounds as organic intermediates, such as monomers corresponding to the next generation photoresist.

BACKGROUND OF THE INVENTION

Fluoroalkanesulfonamide derivatives are compounds useful as organic intermediates. They are compounds that are expected, for example, as monomers corresponding to the next generation photoresist.

It is known that fluoroalkanesulfonamide derivatives or their analogous compounds can be synthesized, for example, by each process of the following Process "a" to Process "d".

[Process "a"]
It is an example (Non-patent Publication 1) in which trifluoromethanesulfonic anhydride

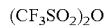(CF$_3$SO$_2$)$_2$O is reacted with 1-bicyclo[2,2,1]hept-5-en-2-ylmethaneamine in an anhydrous methylene chloride solvent in the presence of triethylamine as a base.

[Process "b"]
It is an example (Non-patent Publication 2) in which trifluoromethanesulfonic fluoride

CF$_3$SO$_2$F is reacted with 1-bicyclo[2,2,1]hept-5-en-2-ylmethaneamine in an anhydrous methylene chloride solvent in the presence of triethylamine as a base.

[Process "c"]
It is an example (Non-patent Publication 2) of synthesizing trifluoromethanesulfonic anilide by using trifluoromethanesulfonic chloride

CF$_3$SO$_2$Cl as a sulfonation agent, and by reacting this with aniline in the presence of pyridine as a base, in an anhydrous ether solvent.

[Process "d"]
It is an example (Non-patent Publication 1) of synthesizing N-(m-trifluoromethylphenylsulfonyl)-5-aminomethylbicyclo[2.2.1]hept-2-ene by using m-trifluoromethylphenylsulfonic chloride as a sulfonation agent, and by reacting this with 1-bicyclo[2,2,1]hept-5-en-2-ylmethaneamine in the presence of 20% sodium hydroxide solution as a base, in an ether solvent.

Besides, Patent Publications 1-3, etc. are known as reaction examples of forming a [—SO$_2$—NH—] bond by reacting a sulfonic halide containing a trifluoromethyl group with an amine-series compound.

[Non-patent Publication 1] Zhurnal OrganicheskoiKhimii (Russia), (1995), 31 (3), p. 357-64

[Non-patent Publication 2] Journal of Chemical Society, vol. 6 (5), p. 2574-2578 (published in 1957)

[Patent Publication 1] Japanese Patent Application Publication 8-81436

[Patent Publication 2] Japanese Patent Application Publication 11-209338

[Patent Publication 3] International Publication 97/23448 Pamphlet

SUMMARY OF THE INVENTION

As mentioned above, many examples are known as a reaction of forming a [—SO$_2$—NH—] bond by reacting a fluoroalkanesulfonic halide with an amine. However, there is a problem that "a halogen addition reaction to an unsaturated bond" occurs as a side reaction by using a fluoroalkanesulfonic halide as a raw material relative to a sulfonamidation reaction in which a substrate having a polymerizable double bond is involved. For example, when a sulfonamide compound is synthesized by using trifluoromethanesulfonic chloride as a raw material, N-[(6-chlorobicyclo[2,2,1]hept-5-en-2-yl)methyl]-1,1,1-trifluoromethanesulfonamide (a chlorine adduct) represented by the following formula is produced as a by-product by 2% to 3%.

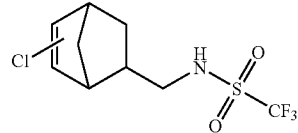

It is not easy to separate this "halogen adduct" from the target product. For example, a rectification using a distillation tower of many stages is necessary for the separation by distillation. The distillation yield is also low, and it is not necessarily advantageous for the production in a large-amount scale.

In contrast with this, there are far less examples of synthesizing a fluoroalkanesulfonamide by reacting "fluoroalkanesulfonic anhydride" with an organic primary amine (the above-mentioned [process "a"]). Since there exist two fluoroalkyl chains (e.g., CF$_3$ groups) in one molecule of fluoroalkanesulfonic anhydride, its unit price is frequently higher as compared with fluoroalkanesulfonic halide. The above-mentioned side reaction (addition reaction), however, does not proceed in the case of using fluoroalkanesulfonic anhydride. As a result of this, the purification load after the reaction is considerably reduced. Particularly, in case that the required purity of the target product is high, it becomes rather advantageous overall. In particular, contamination of a material used for electronic materials with chlorine is not favorable. Therefore, it is very useful to use "fluoroalkanesulfonic anhydride", which does not produce a chlorine adduct as a by-product, upon producing the target product served for such use.

As mentioned above, the above [process "a"] is known as a process for producing fluoroalkanesulfonamide derivatives by using this "fluoroalkanesulfonic anhydride" as a raw material. According to this process, there are merits that the target product can be produced with high selectivity and that by-products difficult of separation are not produced.

However, a main problem of this process is to use a relatively high-price organic base, triethylamine. Furthermore, this base is high in treatment cost, since it must be treated as an organic liquid waste after the reaction. Furthermore, "a triethylamine salt of fluoroalkanesulfonic acid", which is hardly soluble in water and in organic phase, is precipitated as a by-product with the reaction. Therefore, it is essential to have a step of removing the salt by filtration, thereby causing an excessive load on the post-treatment.

In other words, the process using "a fluoroalkanesulfonic anhydride" as a raw material, which is described in Non-patent Publication 1, is a process useful for producing the target product in a small scale to a medium scale. It is, however, still not sufficient in the production in a large-amount scale. Thus, there has been a demand for a further improvement.

In view of such problems, the present inventors have conducted an eager examination in order to establish a production process of fluoroalkanesulfonamide derivatives that is suitable for the production in a large-amount scale.

As a result, we have found that the target fluoroalkanesulfonamide derivative represented by the formula [3] can be produced with high yield by reacting a fluoroalkanesulfonic anhydride represented by the formula [1], with an organic primary amine represented by the formula [2], in the presence of water and in the presence of a base selected from "a hydroxide of an alkali metal or alkaline-earth metal, or a basic salt containing an alkali metal or alkaline-earth metal", thereby reaching the present invention.

In the present invention, a base selected from "a hydroxide of an alkali metal or alkaline-earth metal, or a basic salt containing an alkali metal or alkaline-earth metal" corresponds to a substance that is generally known as "an inorganic base". Herein, "a basic salt containing an alkali metal or alkaline-earth metal" is a salt of an alkali metal hydroxide or alkali-earth metal hydroxide with "a weak acid or midrange acid" such as acetic acid, propionic acid, boric acid, phosphoric acid, and carbonic acid. It refers to one showing basicity (it refers to one showing a pH value of 8 or greater, when an aqueous solution, for example, having a concentration of 0.1 mol·dm$^{-3}$ has been prepared). It became possible to greatly reduce the production cost, since it became possible to use such inorganic base.

In the present invention, it is important to make water coexistent in the reaction system. That is, water is made to be coexistent to have a two-phase system (a heterogeneous system). With this, the target reaction turned out to proceed with high yield even in the case of using "an inorganic base". A fluoroalkanesulfonate, which is produced as a by-product with the reaction, is easily soluble in water. Therefore, the load of the purification treatment after the reaction was greatly reduced.

It is generally known that, when an acid anhydride is brought into contact with water, it is easily decomposed into the corresponding acid (carboxylic acid and sulfonic acid) (see, for example, "Kagaku Daijiten" (Kyoritsu Publishing Co.), Vol. 3, p. 997). Therefore, in the case of using a carboxylic anhydride or sulfonic anhydride as a reaction agent, the reaction is conducted only under an anhydrous condition. The above [process "a"] is not an exception to this, either.

However, with respect to the synthesis of a fluoroalkanesulfonamide represented by the formula [3], in the case of using a fluoroalkanesulfonic anhydride as the raw material and the above-mentioned "inorganic base" as the base in accordance with the above [process "a"], the target reaction proceeds with very low yield (see Comparative Examples).

In view of such condition, the present inventors have tried to make water coexistent in the system and have found that the target reaction unexpectedly proceeds with high yield. That is, it has been found that, even if water is coexistent in the system in the present reaction system, "the decomposition of fluoroalkanesulfonic anhydride by water" does not occur significantly, and the target reaction occurs predominantly. As a result, it became possible to remarkably advantageously produce the target fluoroalkanesulfonamide as compared with the conventional techniques.

The present inventors have found that it proceeds still more preferably by conducting the above reaction in a manner to gradually or continuously add either a fluoroalkanesulfonic anhydride represented by the formula [1] or water into the reaction system.

Furthermore, the present inventors have found that the above reaction proceeds still more preferably under a coexistence of a non-aqueous organic solvent. Furthermore, it has been found still more preferable to use particular ones in terms of the type of the above "inorganic base", the amount of water, the type and the amount of the non-aqueous organic solvent, and the like, thereby reaching the completion of the present invention.

According to the present invention, there is provided a first process for producing a fluoroalkanesulfonamide derivative represented by the formula [3],

comprising reacting a fluoroalkanesulfonic anhydride represented by the formula [1], $(R^1R_fSO_2)_2O$            [1]

with an organic primary amine represented by the formula [2],

in the presence of water and in the presence of a base selected from the group consisting of (a) a hydroxide of an alkali metal or alkaline-earth metal or (b) a basic salt containing an alkali metal or alkaline-earth metal, wherein $R_f$ represents a $C_1$-$C_{20}$ perfluoroalkylene group —$(C_aF_{2a})$— where a is an integer of 1-20, $R^1$ represents a fluorine atom, hydrogen atom, or organic functional group optionally containing a double bond, $R_f$ and $R^1$ may be bonded together to form a cyclic structure, and $R^2$ represents an organic functional group containing at least one polymerizable double bond.

The organic primary amine may be defined as being one except 1-bicyclo[2.2.1]hept-5-en-2-ylmethaneamine represented by the following formula:

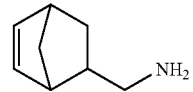

The first process may be a second process in which $R^1$ of the formula [1] represents a fluorine atom, and in which $R^2$ of the formula [2] represents a functional group represented by the formula [4], A-O-$R^{2a}$—            [4]

so that the fluoroalkanesulfonamide derivative is represented by the formula [3a],

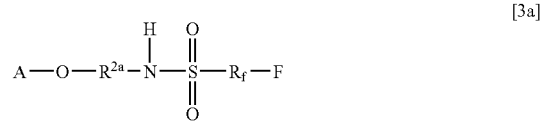

wherein A represents a functional group represented by the formula [4a], [4b] or [4c],

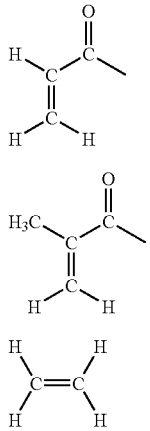

$R^{2a}$ represents an $C_1$-$C_{20}$ alkylene group, $C_5$-$C_{40}$ alicyclic group or $C_5$-$C_{40}$ aromatic group, and carbons of $R^{2a}$ may partially be replaced with nitrogen, oxygen, sulfur, fluorine, chlorine, bromine, or iodine.

The first process may be a third process in which "$R^1R_f$" of the formula [1] represents a trifluoromethyl group, and in which $R^2$ of the formula [2] represents a functional group represented by the formula [5],

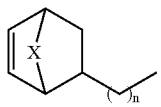

[5]

so that the fluoroalkanesulfonamide derivative is represented by the formula [3b],

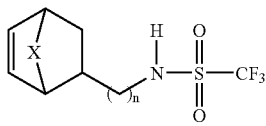

[3b]

wherein X represents —$CH_2$—, —O— or —S—, and n represents an integer of 0-6. When X represents —$CH_2$—, n may represent an integer of 2-6.

DETAILED DESCRIPTION

According to the present invention, it is possible to produce a fluoroalkanesulfonamide derivative represented by the formula [3] with high yield from raw materials of low prices. It is possible to use "an inorganic base". Therefore, the operational load after the reaction, such as liquid waste treatment, is also reduced. It is useful for producing the target compound in a large-amount scale.

According to the process of the present invention, it is not necessary to use halogenated hydrocarbons, such as methylene chloride, which are hazardous substances, and the like. It is possible to delete a step of removing the salt by filtration.

This also makes the operation easy. Therefore, it is a particularly useful process to produce the target product in an industrial scale.

In the following, the present invention is explained in more detail. The present invention is achieved by reacting a fluoroalkanesulfonic anhydride represented by the formula [1], with an organic primary amine represented by the formula [2], in the presence of water and in the presence of a base selected from "a hydroxide of an alkali metal or alkaline-earth metal, or a basic salt containing an alkali metal or alkaline-earth metal". Although its reaction conditions are described in the following, they do not interfere with the changes of the reaction conditions to the extent that a skilled person can easily adjust them.

$R_f$ in a fluoroalkanesulfonic anhydride represented by the formula [1] represents a $C_1$-$C_{20}$ perfluoroalkylene group [—($C_aF_{2a}$)—; a is an integer of 1-20]. In particular, one having a carbon number of 1-6 is preferable, particularly preferably 1-2 in carbon number. On the other hand, $R^1$ represents an organic functional group optionally having fluorine atom, hydrogen atom or double bond. In particular, it is particularly preferable that $R_fR^1$ are combined together to be a trifluoromethyl group. In this case, the compound of the formula [1] is trifluoromethanesulfonic anhydride. In case that $R^1$ is one other than fluorine or hydrogen, it is an organic functional group optionally having a double bond. This organic functional group may have a hetero atom, such as O, S, N and F, and may have a cyclic structure. Specifically, adamantyl group, —(CO)—O—$R^a$ group (Herein, $R^a$ represents a $C_1$-$C_6$ straight-chain, branched-chain or cyclic alkyl group, or the following functional group),

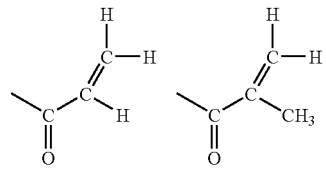

and —$CH_2CH_2$—O—$R^a$ (herein $R^a$ is the same as above) are particularly preferable, in view of the usefulness of the product.

Compounds that can preferably be used as the compound represented by the formula [1] are enumerated in the following.

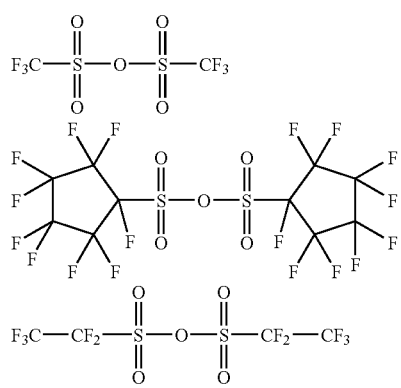

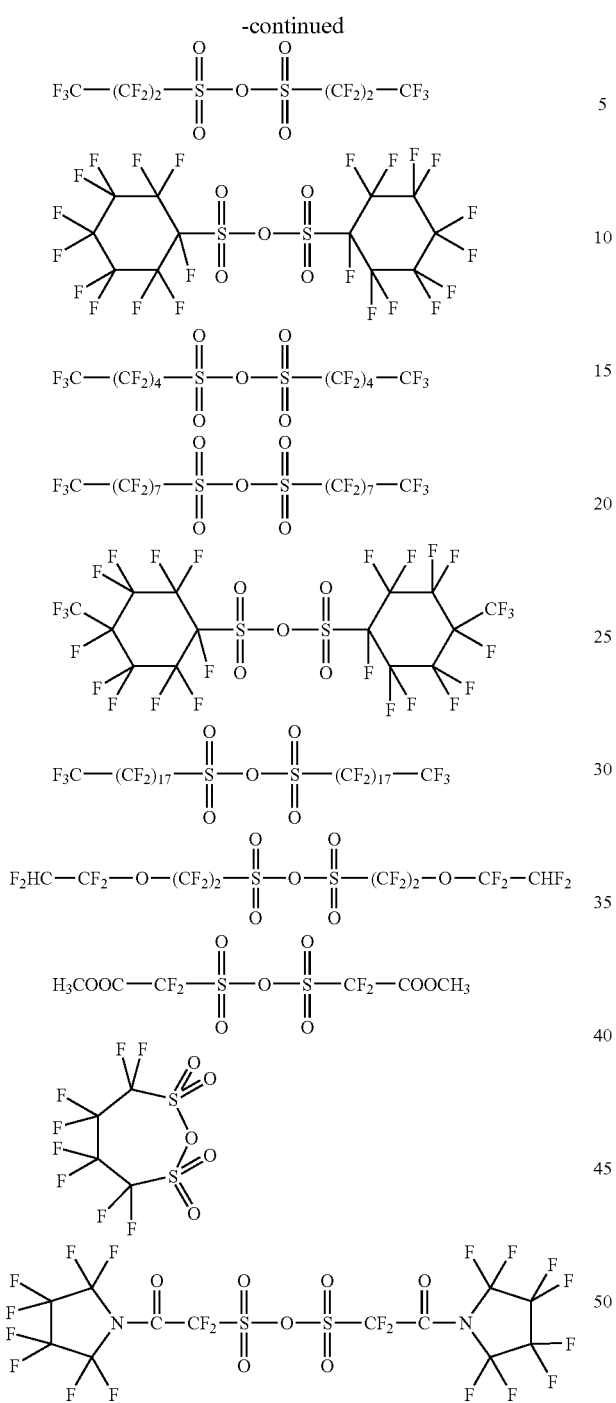

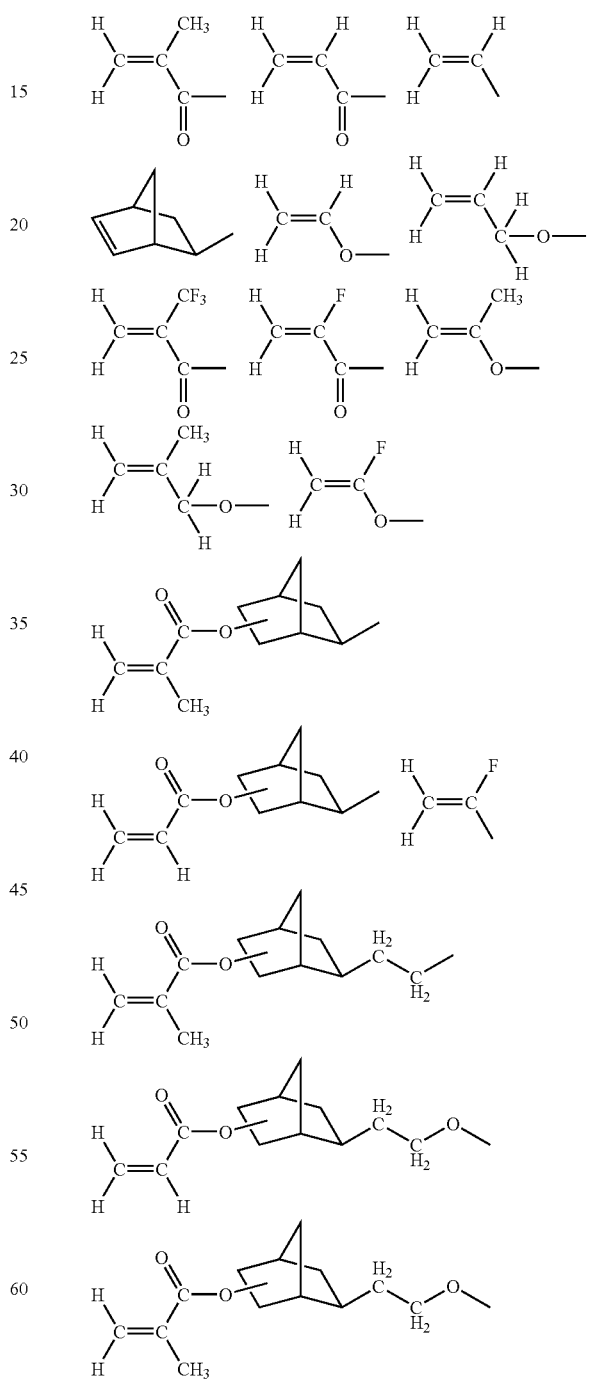

$R^2$ of an organic primary amine represented by the formula [2] is an organic functional group having a polymerizable double bond(s) at one or more positions. As already mentioned, when a fluoroalkanesulfonic halide is reacted with a substrate having a polymerizable double bond, an addition reaction to the double bond site tends to occur. However, the use of fluoroalkanesulfonic anhydride does not cause such a side reaction. Therefore, it is industrially advantageous. Herein, it is possible to cite aryl group, acrylic group, methacrylic group, vinyl group, norbornenyl group, and the like as "the polymerizable double bond group". As $R^2$, groups in which these polymerizable double bond groups are directly bonded to N atoms of the organic primary amines, and groups in which the polymerizable double bond groups are bonded to N atoms through alkylene groups (These alkylene groups are straight chain or branched chain and a part or the entirety of them may form a ring(s). Normally, the carbon number is 1-25, preferably 1-12. A part of the carbon atoms constituting the alkylene group may be replaced with an oxygen or sulfur atom(s)). For example, it is possible to enumerate the following groups.

A compound that can preferably be used as the compound represented by the formula [2] is enumerated in the following.

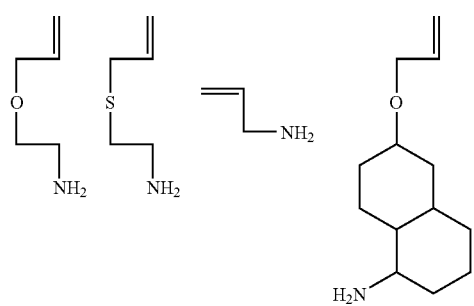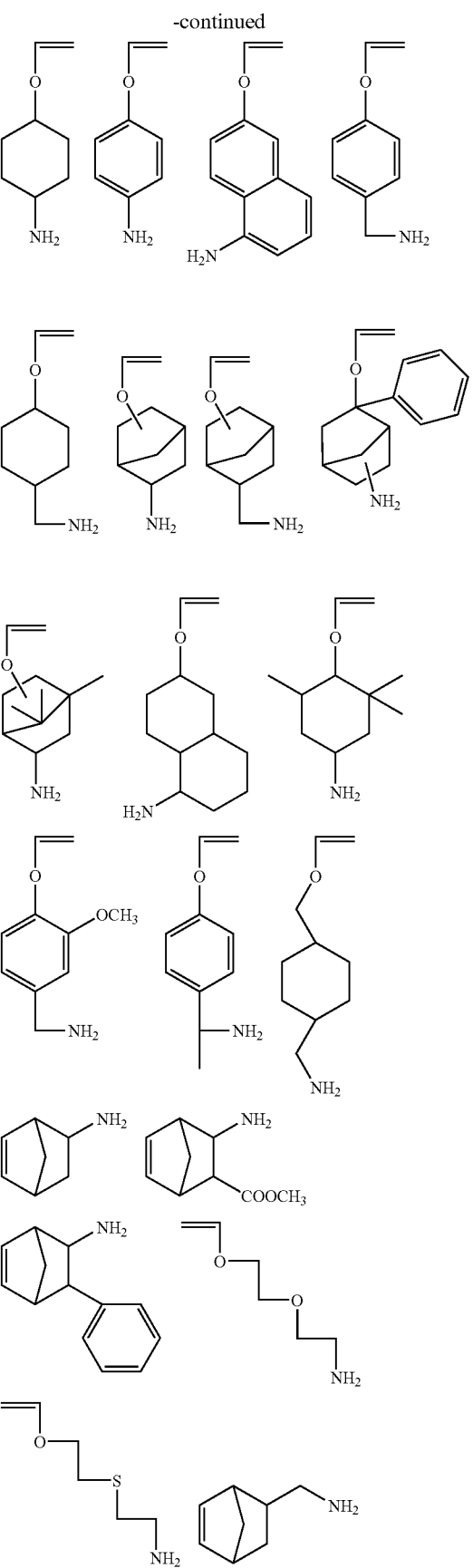

-continued
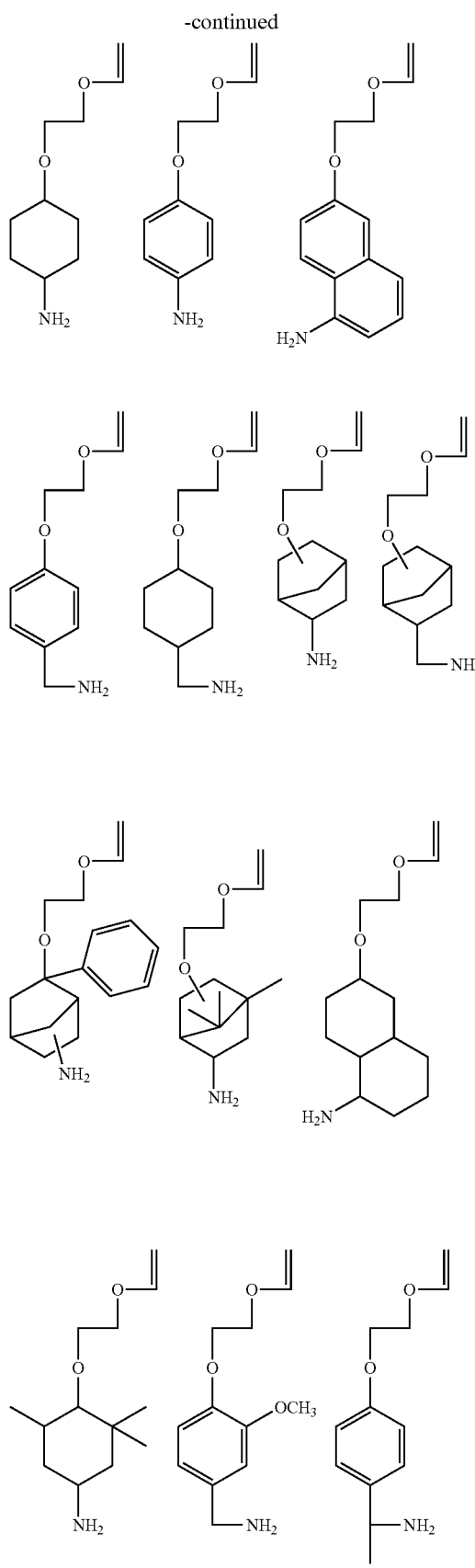
-continued
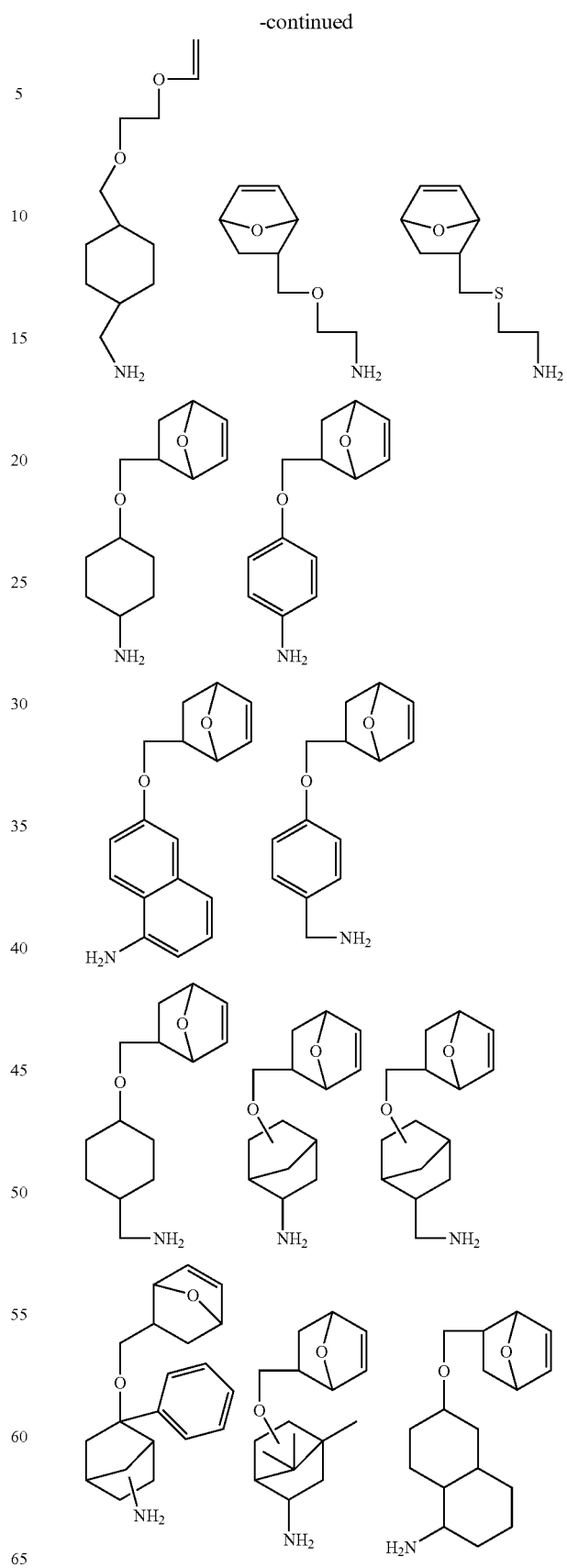

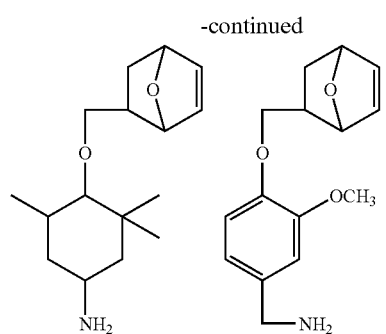
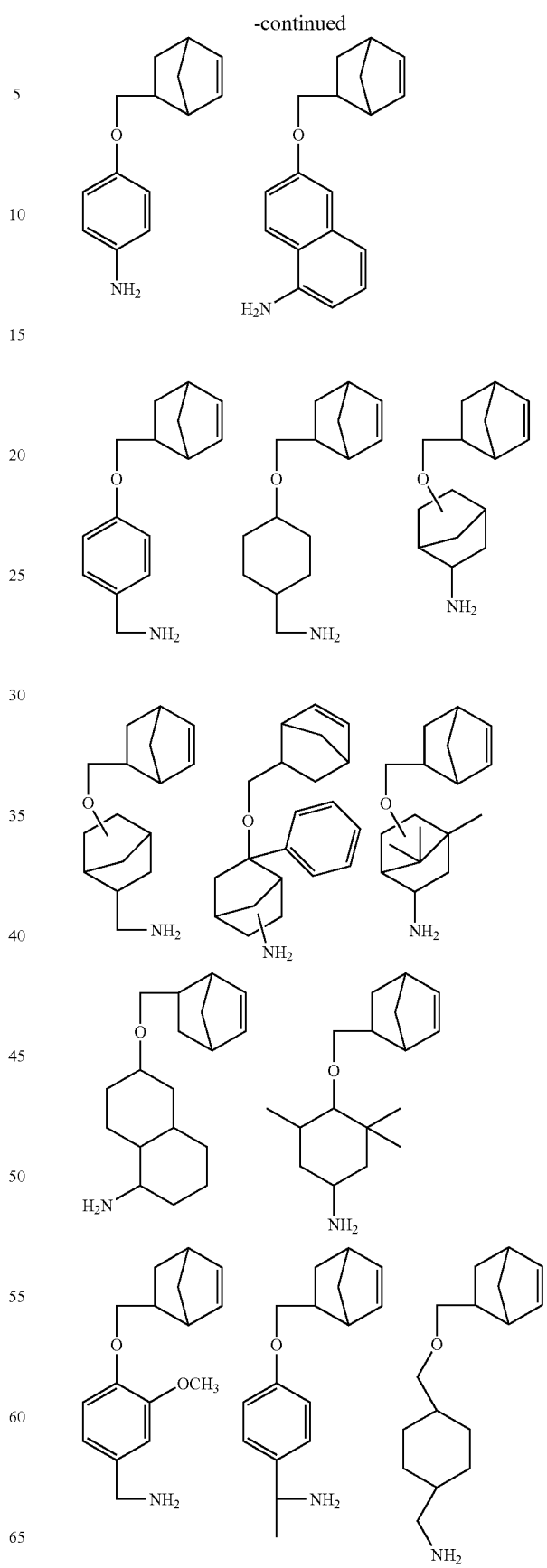

-continued
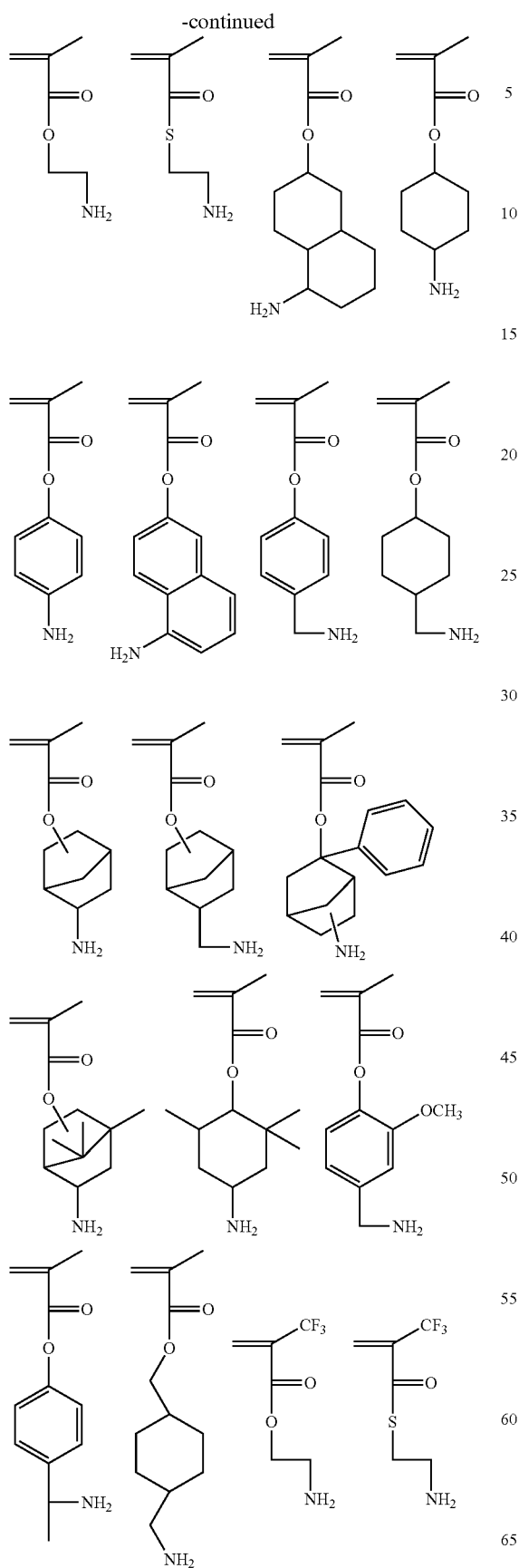
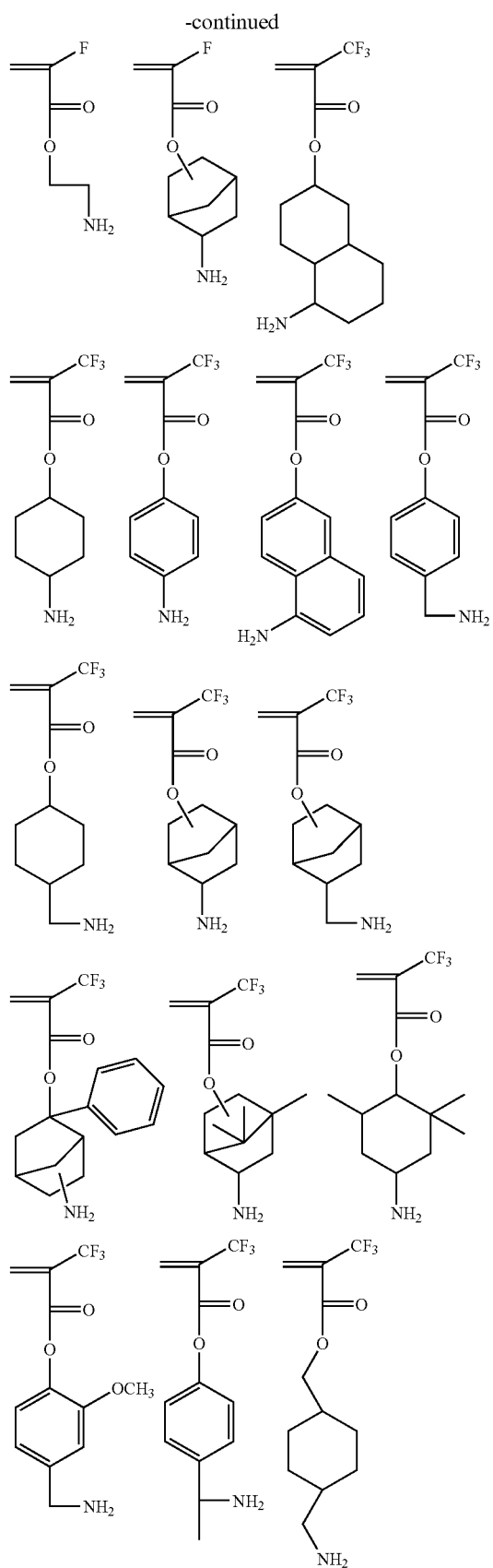

-continued
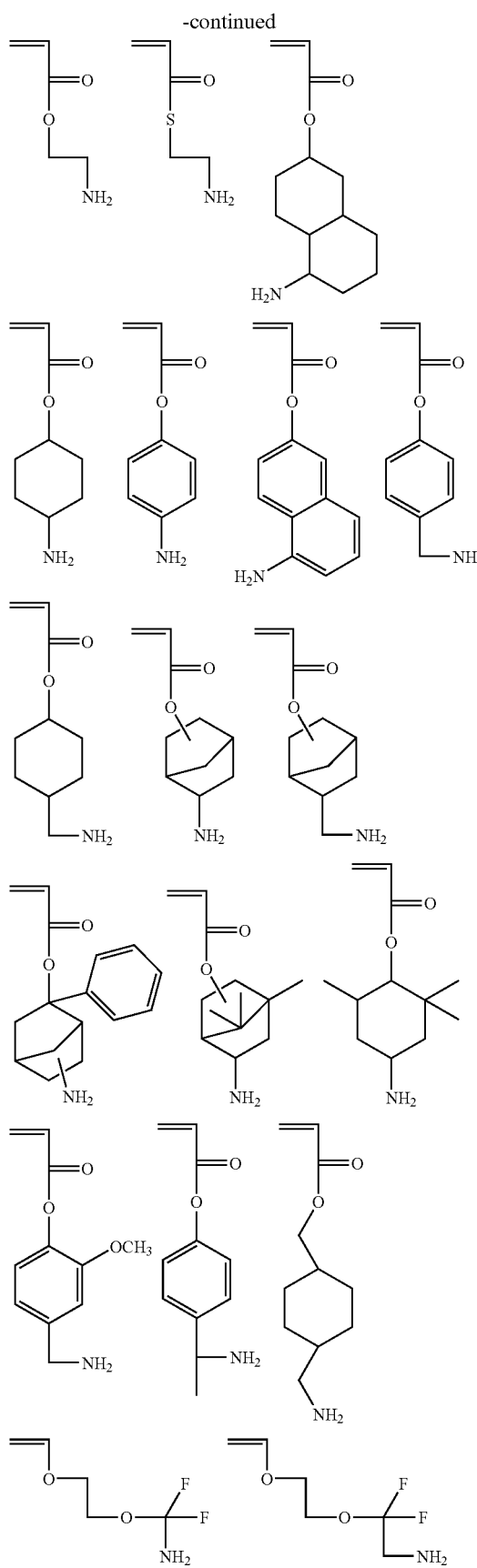
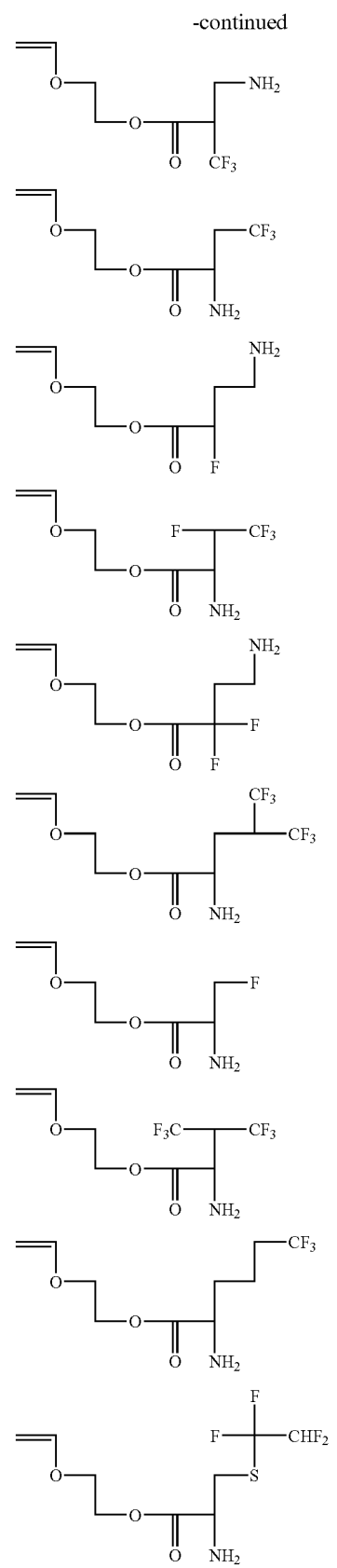

-continued
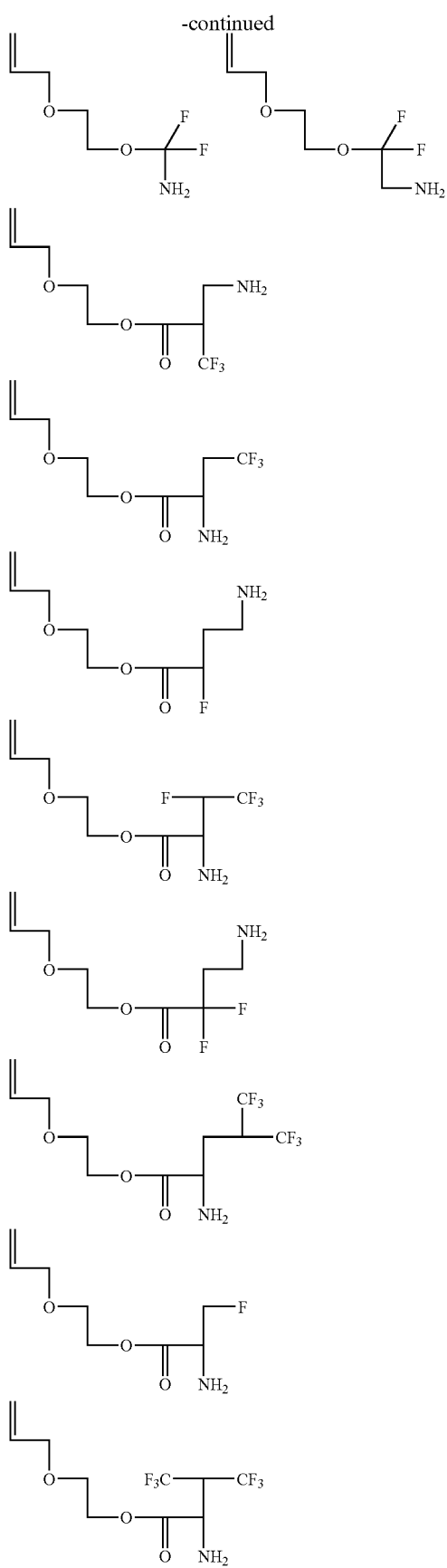
-continued
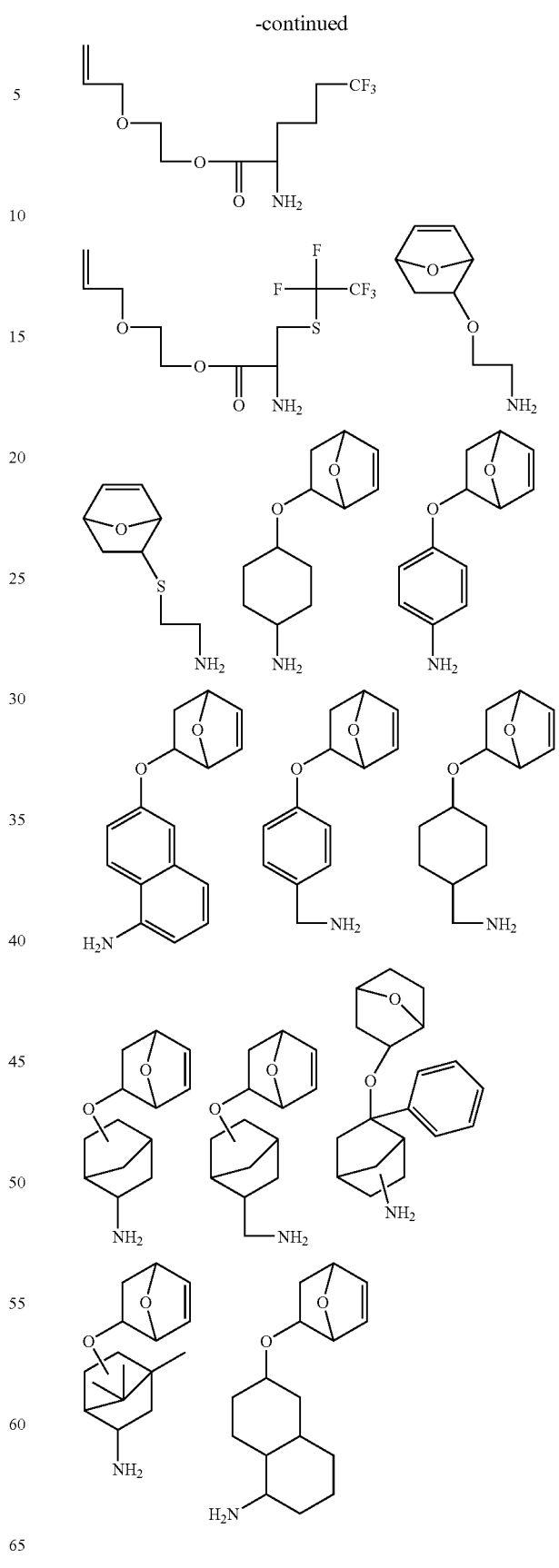

-continued
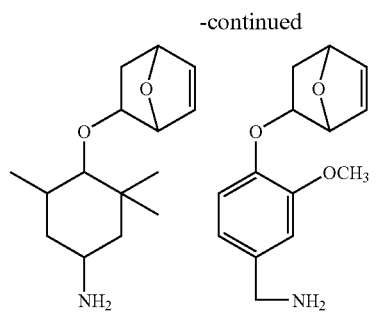
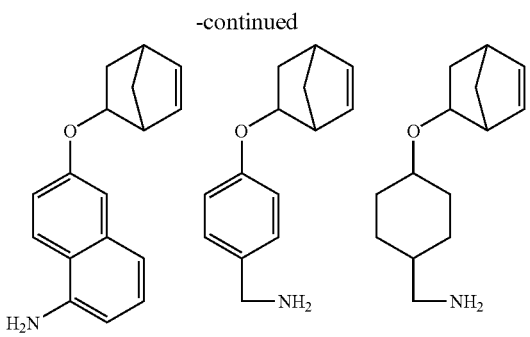
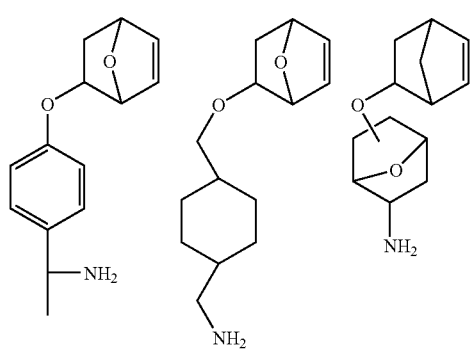
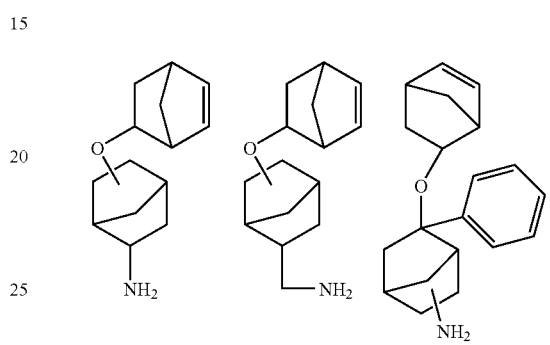
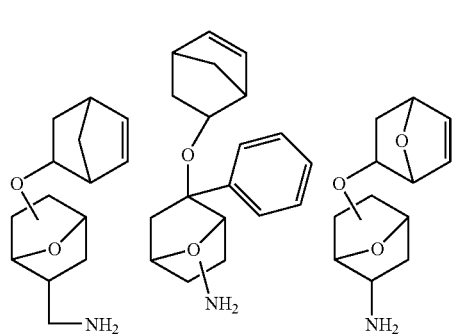
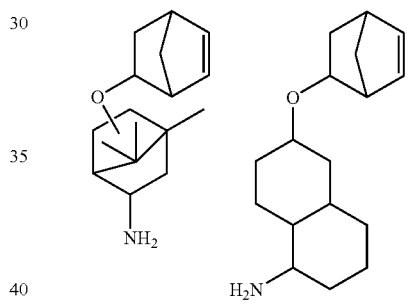
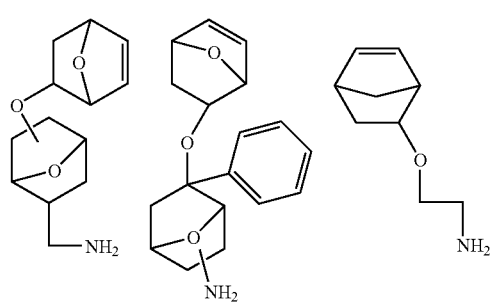
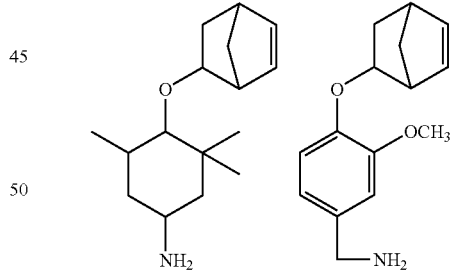
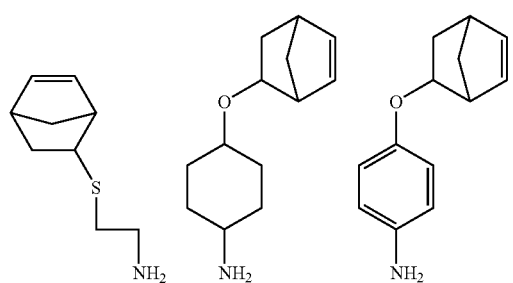
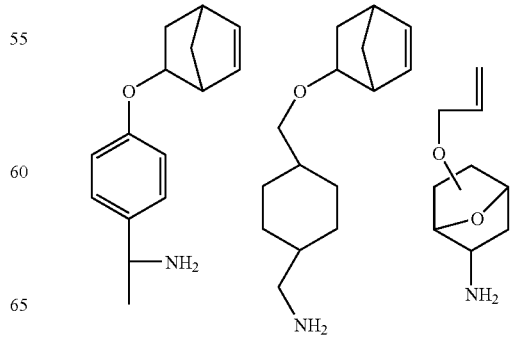

-continued
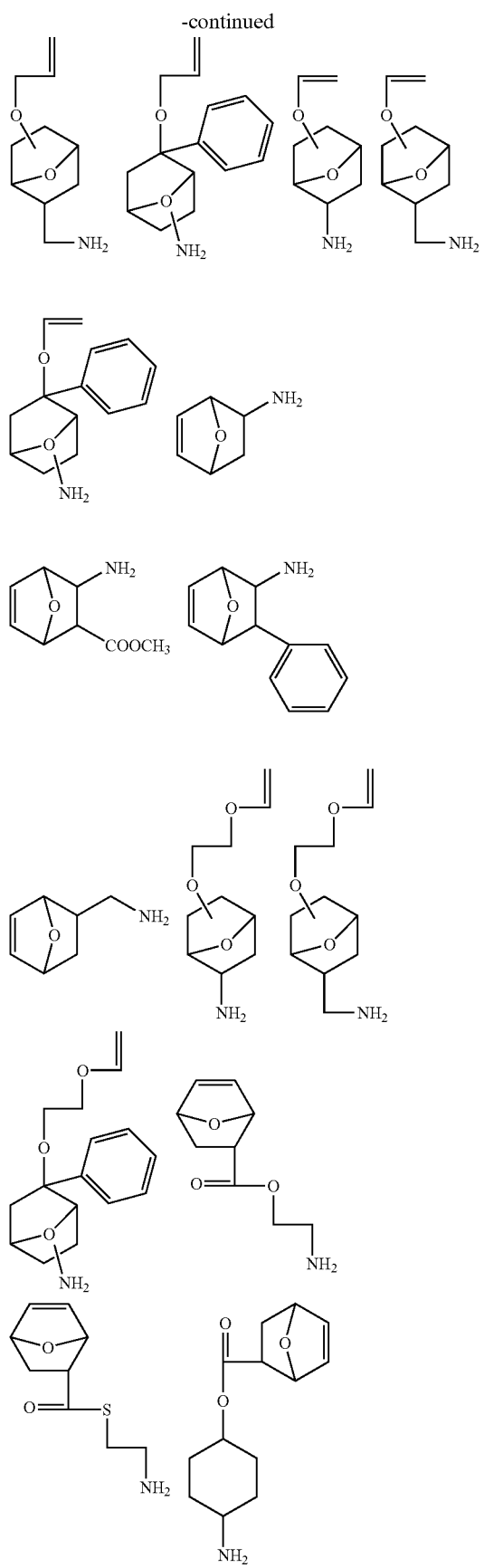
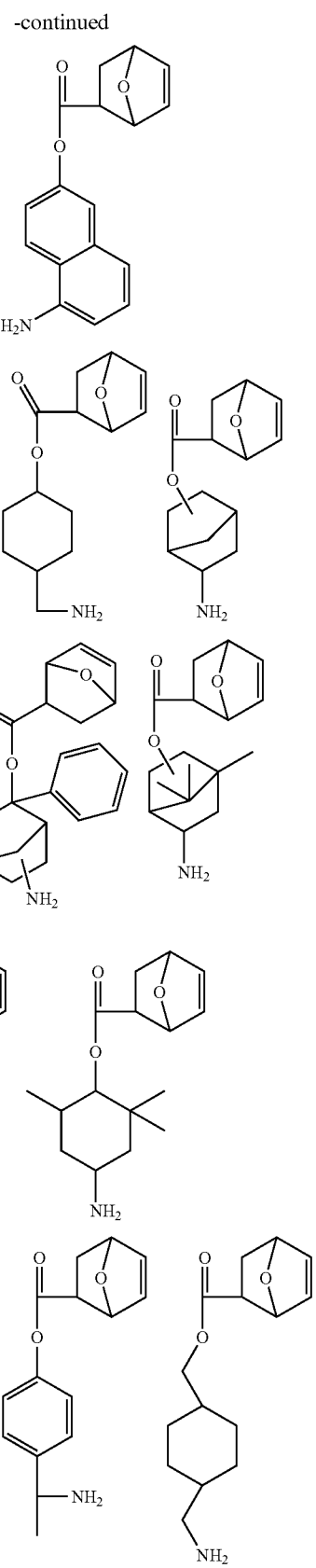

-continued
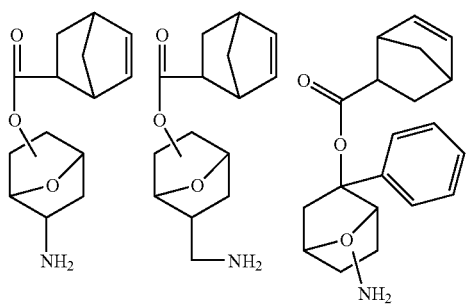
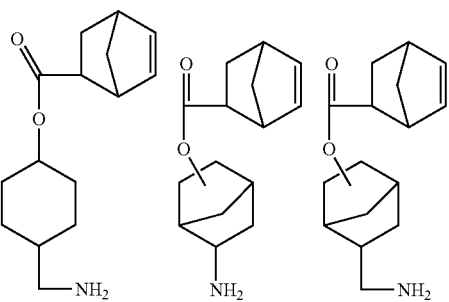
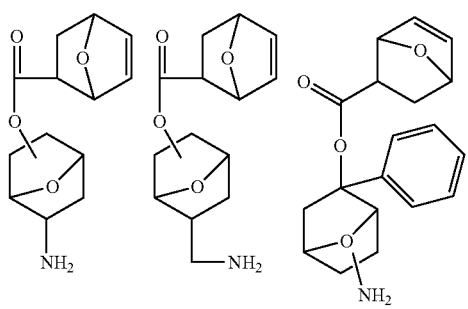
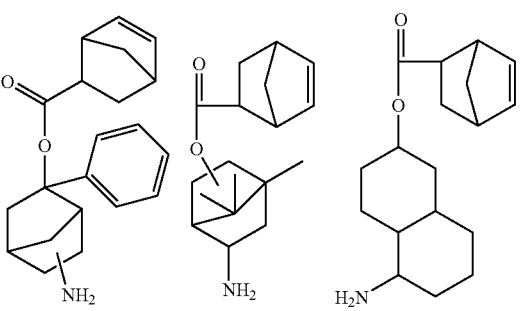
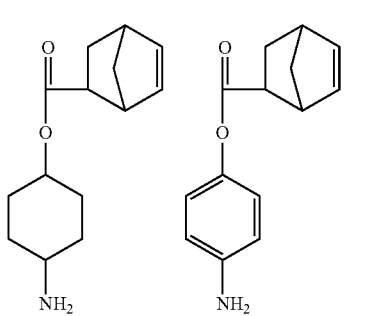
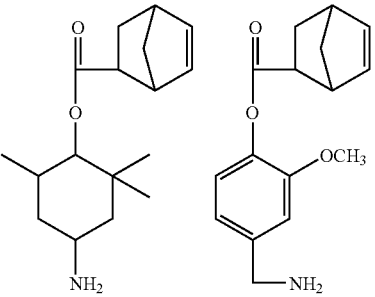
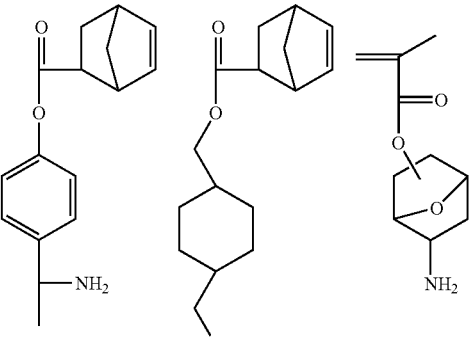
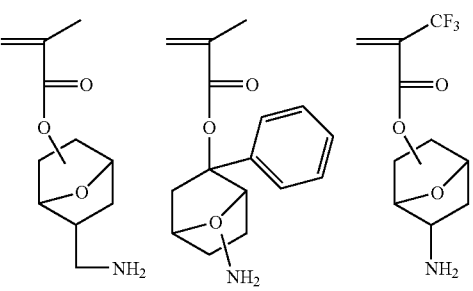

-continued
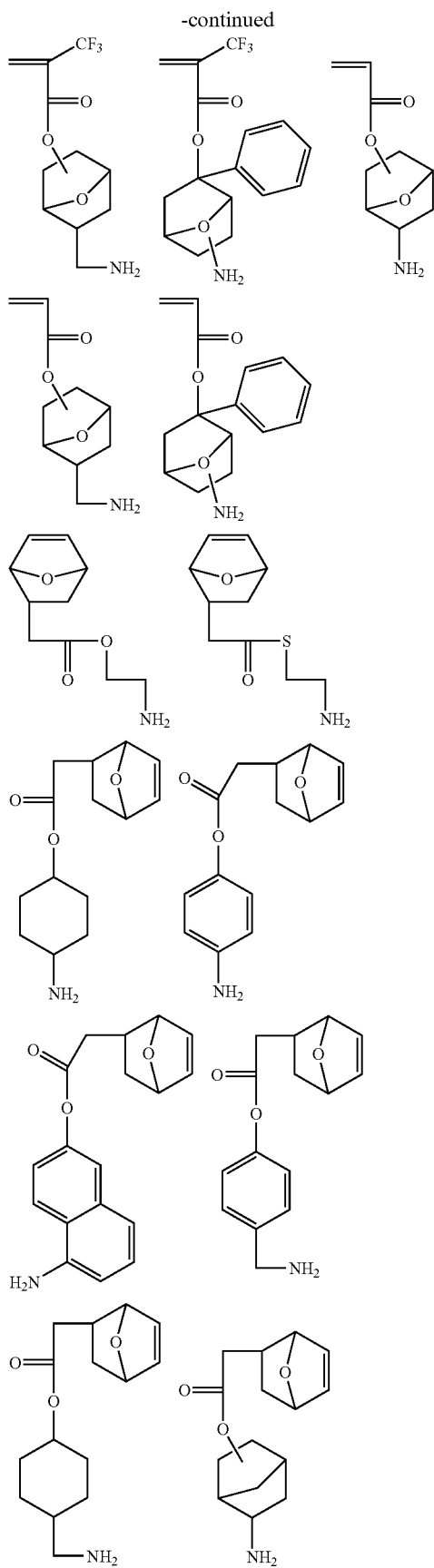
-continued
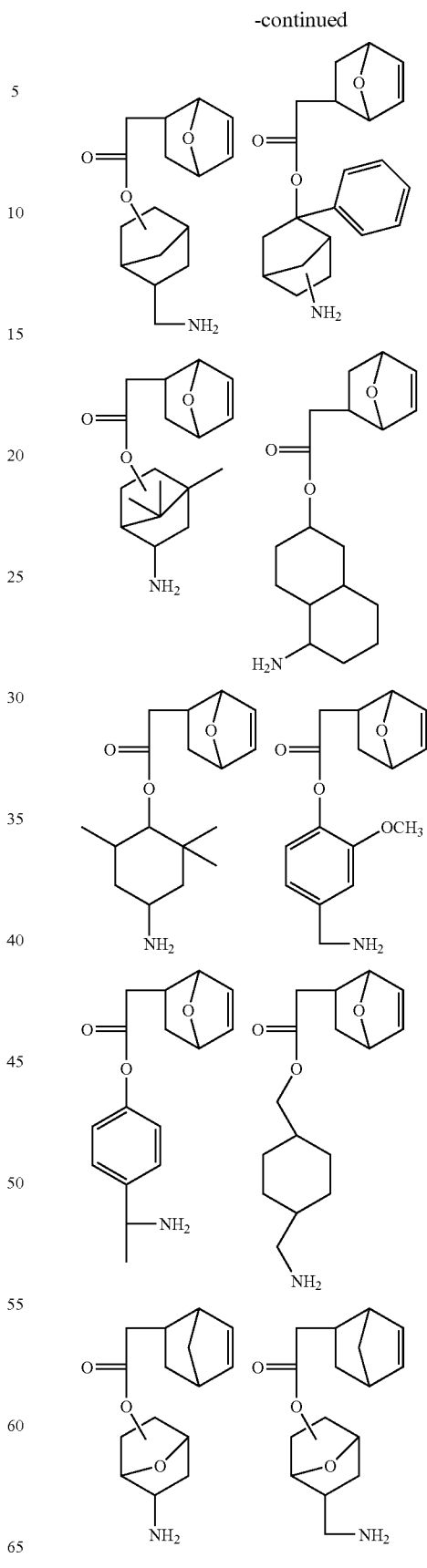

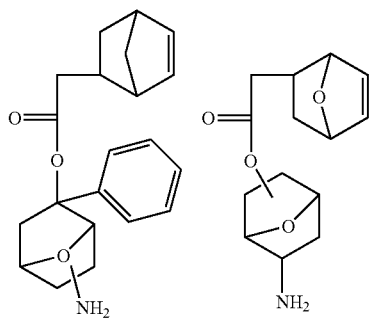
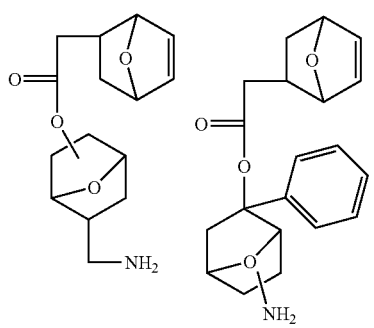
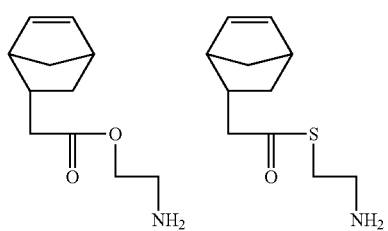
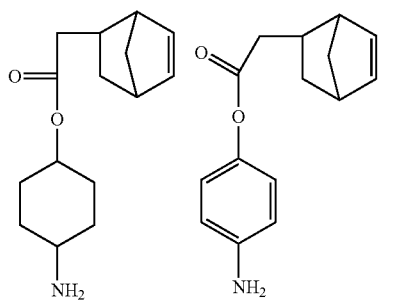
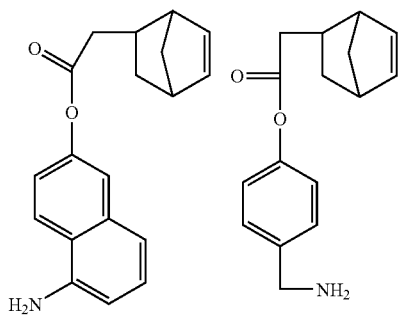
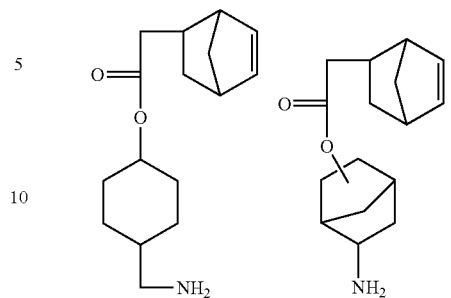
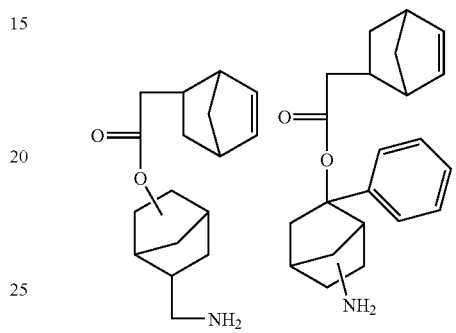
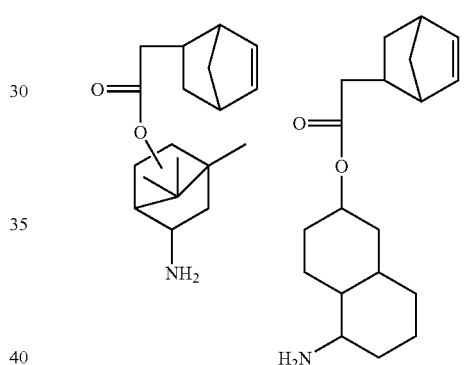
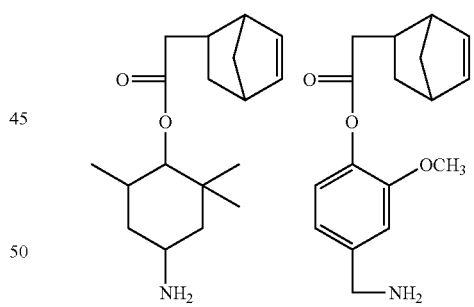
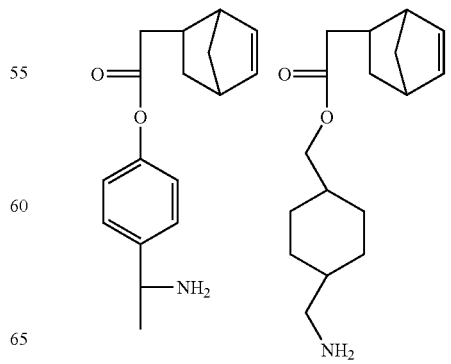

-continued
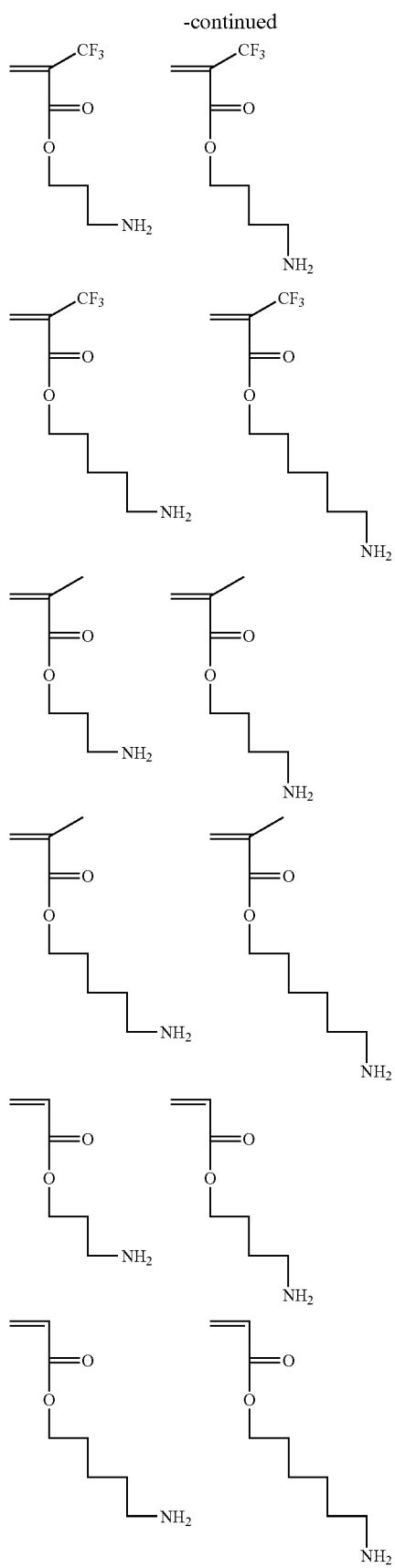
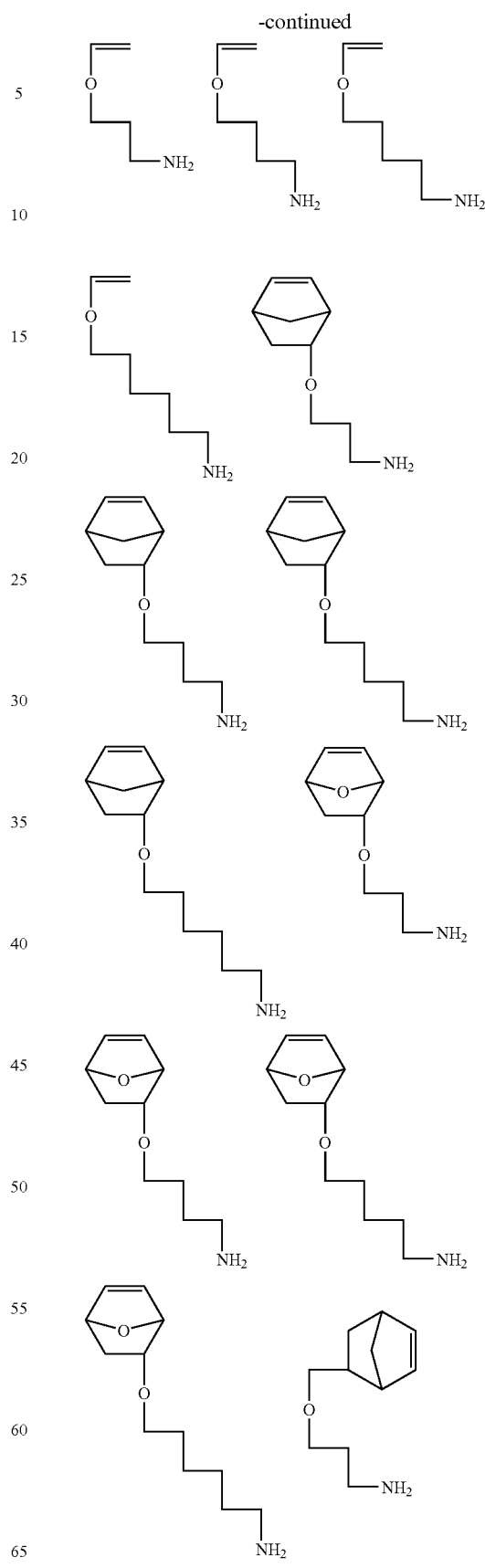

-continued

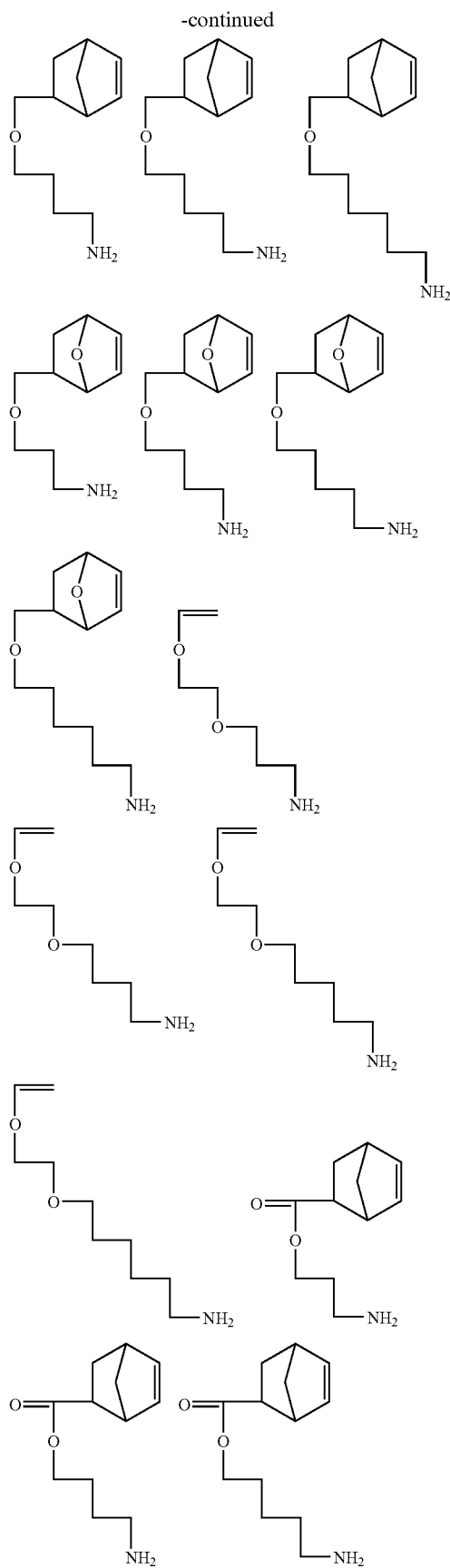

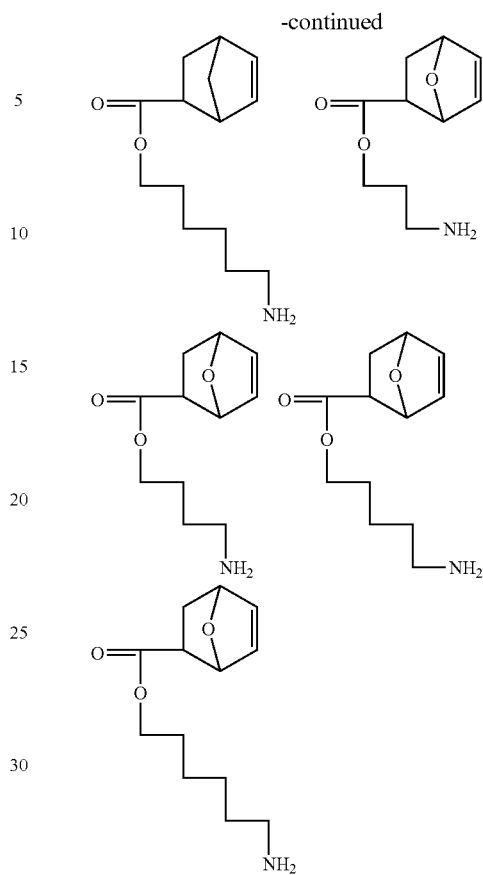

In the present invention, a fluoroalkanesulfonamide derivative represented by the formula [3a], in which $R^1$ is a fluorine atom and $R^2$ is a functional group represented by the formula [4], is a preferable example, due to the usefulness of the product. Herein, $R^{2a}$ is an $C_1$-$C_6$ alkylene group, $C_5$-$C_{40}$ alicyclic group or $C_5$-$C_{40}$ aromatic group, particularly preferably $C_1$-$C_3$ alkylene group, $C_5$-$C_{20}$ alicyclic group and $C_5$-$C_{20}$ aromatic group.

Furthermore, a fluoroalkanesulfonamide derivative represented by the formula [3b], in which [Rf—$R^1$] is a trifluoromethyl group and $R^2$ is a functional group represented by the formula [5], is also a particularly preferable example, due to the usefulness of the product. n is an integer of 0-6, preferably an integer of 2-6, particularly preferably that of 2.

(Reaction Mode)

It is easy and advantageous to conduct the process of the present invention by a batch-type reaction apparatus.

It is possible to minimize the contact between fluoroalkanesulfonic anhydride and water by conducting a manner to gradually add or continuously add either fluoroalkanesulfonic anhydride or water into the reaction system. This is preferable, since it is possible to suppress the decomposition reaction into fluoroalkanesulfonic acid, which is an unnecessary side reaction. As mentioned above, the production of the target compound fluoroalkanesulfonamide antecedes the decomposition reaction into trifluoromethanesulfonic acid in the reaction system of the present invention. Therefore, it is possible to obtain the target product even if such gradual or continuous addition manner is not taken. However, it is possible to improve yield of the target product and it also becomes easy to control the reaction by taking the gradual or continuous addition manner. Therefore, it is particularly preferable in the present invention to gradually add or continuously add either fluoroalkanesulfonic anhydride or water into the reaction system and to adjust the addition rate while measuring the progress condition of the reaction and the temperature of the reaction system. In particular, a method of gradually or continuously adding fluoroalkanesulfonic anhydride is preferable.

(Mixing Ratio of Raw Materials)

There is no particular limitation in the mixing ratio of fluoroalkanesulfonic anhydride represented by the formula [1] to organic primary amine represented by the formula [2], which are the starting raw materials used in the present invention. It is, however, the reaction with a molar ratio of 1:1. Therefore, it is preferable to mix both at around equimolar ratio (1:1). Specifically, the fluoroalkanesulfonic anhydride is in generally 0.5 moles to 2 moles, preferably 0.9 moles to 1.5 moles, more preferably 1 mole to 1.2 moles, relative to 1 mol of the organic primary amine. If it is less than 0.5 moles, the organic primary amine that is not involved in the reaction increases. With this, it is economically disadvantageous. Furthermore, the coloring may occur after the reaction, and it may cause a load on purification. If it exceeds 2 moles, the fluoroalkanesulfonic anhydride that is not involved in the reaction increases. This is economically not preferable due to disposal work.

(Regarding Base)

As the base usable in the present invention, it is possible to cite "a hydroxide of an alkali metal or alkaline-earth metal, or a basic salt containing an alkali metal or alkaline-earth metal" such as alkali metal hydroxides and alkali-earth metal hydroxides, such as lithium hydroxide, sodium hydroxide, potassium hydroxide, magnesium hydroxide, calcium hydroxide and barium hydroxide, lithium carbonate, potassium carbonate, sodium carbonate, lithium hydrogencarbonate, sodium hydrogencarbonate, sodium acetate, potassium acetate, disodium hydrogenphosphate, and dipotassium hydrogenphosphate. Of these, sodium carbonate, potassium carbonate, sodium hydroxide, and potassium hydroxide are particularly preferable, due to their economy, handling easiness, high reactivity as the base, etc.

The amount of the base used in the present reaction is, in case that it is a monovalent base, in 0.2 moles to 2 moles, preferably 0.5 moles to 1.5 moles, more preferably 0.9 moles to 1.2 moles, relative to 1 mol of the organic primary amine of the substrate. If the amount of the base is less than 0.2 moles relative to 1 mol of the organic primary amine of the substrate, both of selectivity of the reaction and yield of the target product lower. If it exceeds 2 moles, it is economically not preferable due to the increase of the base that is not involved in the reaction. These quantitative relationships are inversely proportional to the valence of the base. For example, it is a half of this in the case of a bivalent base.

(Regarding the Amount of Water)

In the present invention, it is necessary to make water coexistent in the reaction system in order to achieve the increase of the reactivity. By making water coexistent, a fluoroalkanesulfonate that precipitates with the reaction is dissolved in the aqueous phase. Therefore, in contrast with Non-patent Publication 1, it is possible to avoid "precipitation of a hardly soluble salt", and operability is remarkably improved.

The amount of water to be coexistent is in normally 0.2 g to 100 g (20 wt % to 10,000 wt %), preferably 1 g to 10 g (100 wt % to 1,000 wt %), more preferably 2 g to 6 g (200 wt % to 600 wt %). If the amount of water to be coexistent is less than 0.2 g (20 wt %) relative to 1 g of the organic primary amine, the degree of yield improvement is small, and it is difficult to obtain the advantageous effect of specially adding water. In contrast with this, if the amount of water is in 1 g (100 wt %) or greater, more preferably 1.5 g (150 wt %) or greater, more preferably 2 g (200 wt %) or greater, it is possible to dissolve a sufficient amount of the inorganic base used in the present invention and to secure a high reactivity. Furthermore, it is possible to more securely dissolve a fluoroalkanesulfonate that is produced as a by-product with the reaction. It is greatly advantageous to use such an excessive amount of water, particularly in the case of conducting the reaction in a large-amount scale. Therefore, it is still more preferable that the amount of water is in 1.5 g to 6 g, particularly 2 g to 6 g (200 wt % to 600 wt %) to conduct the present invention. The present invention is characterized in that, even such a large excess of water is made to be coexistent in the system, the reaction of the fluoroalkanesulfonic anhydride with water does not occur significantly, and the reaction with the organic primary amine is greatly accelerated.

On the other hand, if the amount of water exceeds 100 g, it is economically not preferable from the viewpoint of productivity.

(Regarding Non-Aqueous Organic Solvent)

In the present reaction, it is preferable to make a non-aqueous organic solvent further coexistent in the system for the purpose of improving yield and making easy a separation between the produced target product and a fluoroalkanesulfonate aqueous solution produced as a by-product.

The type of the non-aqueous organic solvent usable is not particularly limited. It is possible to use saturated hydrocarbons, such as pentane, hexane and heptane; aromatic compounds, such as benzene, toluene, xylene and mesitylene; ether compounds, such as diethyl ether, methyl-t-butyl ether, diisopropyl ether, and tetrahydrofuran; halogenated hydrocarbons, such as methylene chloride, chloroform, and carbon tetrachloride. These may be used singly, or a plurality of solvents may be used together. Furthermore, as mentioned above, methylene chloride was used in Non-patent Publication 1. In the present invention, however, there is an advantage that the reaction proceeds well even if such halogenated hydrocarbon is not used. To further use the advantage, it is still more preferable in the present invention to use toluene, xylene, pentane, hexane, diisopropyl ether and the like, which are less in environmental load, as compared with halogenated hydrocarbons, benzene and the like.

In the case of using a non-aqueous organic solvent in the present reaction, its amount is normally 0.5 g to 100 g, preferably 1 g to 10 g, more preferably 2 g to 5 g, relative to 1 g of the organic primary amine. If the amount of the solvent is 1 g, particularly, 2 g or greater, a good two-phase system is formed by an aqueous phase in which an inorganic base is dissolved and an organic phase in which the reactants are dissolved. This is good from the viewpoint of yield of the target product. On the other hand, if the amount of the solvent is less than 0.5 g relative to 1 g of the organic primary amine, an operability problem, such as difficulty of separating the two layers after the reaction, may occur. If it exceeds 100 g, it is economically not preferable from the viewpoint of productivity.

To conduct the present invention, it is a preferable combination that water is in 1 g to 10 g and the non-aqueous organic solvent is in 1 to 10 g, relative to 1 g of the organic primary amine. It is a particularly preferable combination that water is in 2-6 g and the non-aqueous organic solvent is in 2-5 g.

(Regarding Temperature)

The reaction temperature upon conducting the present invention is normally −20° C. to 100° C., preferably −15° C. to 70° C., more preferably −10° C. to 50° C. If it is lower than −20° C., operability lowers since water in the reaction system solidifies in some cases. If it exceeds 100° C., the product decomposition and the like may occur. Therefore, it is not preferable.

(Regarding the Reactor)

The reactor for conducting the reaction of the present invention is not particularly limited. Both of the closed system and the open system can be used. As the material, one lined with tetrafluoroethylene resin, chlorotrifluoroethylene resin, vinylidene fluoride resin, PFA resin, glass or the like, a glass container, or one made of stainless steel is preferable.

Although the process for conducting the present invention is not limited, one example of desirable embodiments is described in detail. A reactor proof against the reaction conditions is charged with a base, a solvent, and an organic primary amine of the raw material. While controlling the temperature from outside, a fluoroalkanesulfonic anhydride is added, followed by stirring. It is preferable to confirm that the reaction has terminated by monitoring the consumption of the raw material by sampling or the like.

(Regarding Purification Method)

It is possible to purify a fluoroalkanesulfonamide that is represented by the formula [3] and has been produced by the process of the present invention, by applying a known method.

After conducting the reaction of the present invention, the target product fluoroalkanesulfonamide exists in the organic phase (a phase formed of the unreacted raw materials, the non-aqueous organic solvent and the like), and a fluoroalkanesulfonate produced as a by-product exists in the aqueous phase. Therefore, it is possible to easily remove the fluoroalkanesulfonate to the outside of the system by subjecting the reaction liquid to a two-layer separation. Then, it is washed with water, followed by distilling the solvent off, thereby obtaining a crude organic matter. The obtained crude organic matter does not contain by-products that are difficult in separation. Therefore, it is possible to easily obtain the fluoroalkanesulfonamide of high purity by conducting a purification such as column chromatography, distillation or the like.

In the present invention, the first process may be a fourth process for producing a fluoroalkanesulfonamide derivative represented by the formula [3]. The fourth process includes the sequential steps of:

(a) charging a reactor with (i) an organic primary amine represented by the formula [2], (ii) 0.2-100 g of water per gram of the organic primary amine, (iii) 0.5-100 g of a non-aqueous organic solvent per gram of the organic primary amine, and (iv) a base that is at least one selected from the group consisting of lithium hydroxide, sodium hydroxide, potassium hydroxide, magnesium hydroxide, calcium hydroxide, barium hydroxide, potassium carbonate, sodium carbonate, sodium hydrogencarbonate, sodium acetate, potassium acetate, disodium hydrogenphosphate, and dipotassium hydrogenphosphate; and (b) intermittently or continuously introducing a fluoroalkanesulfonic anhydride represented by the formula [1], into the reactor at a temperature of −10° C. to 50° C., thereby reacting the fluoroalkanesulfonic anhydride with the organic primary amine.

According to the fourth process, it is possible to produce the fluoroalkanesulfonamide derivative with a particularly high yield and an operational advantage.

In particular, it is possible to cite an embodiment in which the reactor is previously charged with the reaction reagents other than the fluoroalkanesulfonic anhydride, and the reaction is conducted by gradually or continuously introducing the fluoroalkanesulfonic anhydride thereinto, in which the type of the base is selected from the group consisting of sodium carbonate, potassium carbonate, sodium hydroxide, and potassium hydroxide, in which 2 g to 6 g of water and 2 g to 5 g of the non-aqueous organic solvent are made to be coexistent at the reaction per gram of the organic primary amine, and in which the reaction temperature is −10° C. to 50° C., as a particularly superior one.

Although the present invention is described in detail by examples in the following, it is not limited to these embodiments. Herein, "%" of the composition analysis value represents "areal %" of an organic component except the solvent component, which has been obtained by sampling a part of the reaction mixture and by measuring it by gas chromatography.

EXAMPLE 1

A 1 L, four-necked flask equipped with a dropping funnel and a stirring apparatus was charged with 100 g of heptane, 17.9 g (0.45 moles) of sodium hydroxide, 200 g (11.1 moles) of water, and 51.3 g (0.41 moles) of an organic primary amine represented by the following formula,

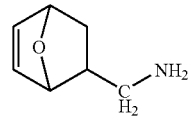

followed by stirring. When the inside temperature became not higher than 10° C. by an outside cooling apparatus, 114 g (0.41 moles) of trifluoromethanesulfonic anhydride were added from the dropping funnel by spending 1 hr. After the termination of the dropping, stirring was conducted for 1 hr at an inside temperature of 20° C. Then, the composition was measured by gas chromatography. With this, an isomer mixture of the target N-(bicyclo[2,2,1]hept-5-en-2-ylmethyl)-1,1,1-trifluoromethanesulfonamide was in 99.4% in total. Besides, 1-bicyclo[2,2,1]hept-5-en-2-ylmethylmethaneamine of the raw material was detected by 0.6%. The reaction liquid was separated into two layers with a separatory funnel. Then, the organic layer was washed with 100 ml of 5% sulfuric acid aqueous solution, followed by washing two times with 100 ml of water. The solvent was distilled out of the obtained solution, thereby obtaining a crude organic matter. This crude organic matter was subjected to vacuum distillation, thereby obtaining 90.7 g of an isomer mixture of a fluoroalkanesulfonamide of the following formula.

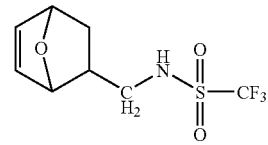

The composition was examined by gas chromatography. With this, purity of the target product, the following fluoroalkanesulfonamide (a mixture of endo product and exo product), was 99.9%. Yield was 86%.

EXAMPLE 2

A 1 L, four-necked flask equipped with a dropping funnel and a stirring apparatus was charged with 100 g of heptane, 17.9 g (0.45 moles) of sodium hydroxide, 200 g of water, and 56.2 g (0.41 moles) of an organic primary amine represented by the following formula,

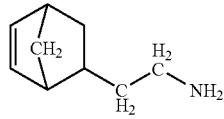

followed by stirring. When the inside temperature became not higher than 10° C. by an outside cooling apparatus, 114 g (0.41 moles) of trifluoromethanesulfonic anhydride were added from the dropping funnel by spending 1 hr. After the termination of the dropping, stirring was conducted for 1 hr at an inside temperature of 50° C. Then, the composition was measured by gas chromatography. With this, an isomer mixture of the target fluoroalkanesulfonamide of the following formula was in 99.9% in total. The reaction liquid was separated into two layers with a separatory funnel. Then, the organic layer was washed with 100 ml of 5% sulfuric acid aqueous solution, followed by washing two times with 100 ml of water.

The solvent was distilled out of the obtained solution, thereby obtaining a crude organic matter. This crude organic matter was subjected to vacuum distillation to collect the distillate, thereby obtaining an isomer mixture of the target product. The composition was examined by gas chromatography. With this, an isomer mixture of the target product, a fluoroalkanesulfonamide of the following formula,

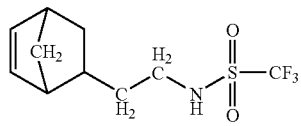

was in 99.9% in total, and others were in 0.2%. Yield was 87%.

COMPARATIVE EXAMPLE 1

The reaction and the post-treatment were conducted under the same conditions as those of Example 1 by using the same raw materials as those of Example 1, except in that the reaction was conducted under no water condition (nitrogen atmosphere) by adding no water. As a result, although an isomer mixture (purity: 99.9%) of the target fluoroalkanesulfonamide was obtained, yield was 40%.

COMPARATIVE EXAMPLE 2

The reaction and the post-treatment were conducted under the same conditions as those of Example 2 by using the same raw materials as those of Example 2, except in that the reaction was conducted under no water condition (nitrogen atmosphere) by adding no water. As a result, although an isomer mixture (purity: 99.8%) of the target fluoroalkanesulfonamide was obtained, yield was 41.5%.

EXAMPLES 3-9 & COMPARATIVE EXAMPLES 3-9

The reactions were respectively conducted in Examples 3-9 and Comparative Examples 3-9 under the same conditions (the conditions in which all of the molar amounts of the reagents, operation, temperature, and time were the same) as those of Example 1 and as those of Comparative Example 1. The obtained results are put together in Table 1.

TABLE 1

| Group ($R^1R_j$) of Compound of Formula [1] | Compound of Formula [2] | Yield | |
|---|---|---|---|
| $CF_3$—$(CF_2)_2$— | (norbornene-CH₂-NH₂ with O bridge) | Example 3 | 85.2% |
| | | Com. Ex. 3 | 39.7% |
| $CHF_2$—$CF_2$—O—$(CF_2)_2$— | (norbornene-CH₂-NH₂ with O bridge) | Example 4 | 82.1% |
| | | Com. Ex. 4 | 41.3% |
| $CF_3$— | (methacrylate-O-norbornyl-NH₂) | Example 5 | 80.5% |
| | | Com. Ex. 5 | 38.6% |

TABLE 1-continued

| Group ($R^1R_f$) of Compound of Formula [1] | Compound of Formula [2] | Yield | |
|---|---|---|---|
| $CF_3$—$(CF_2)_2$— | 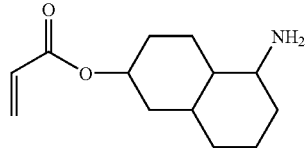 | Example 6<br>Com. Ex. 6 | 80.5%<br>38.6% |
| $CF_3$—$(CF_2)_7$— | 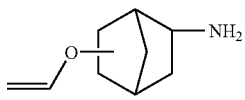 | Example 7<br>Com. Ex. 7 | 81.4%<br>42.2% |
| $CF_3$—$(CF_2)_2$— | 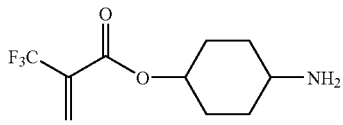 | Example 8<br>Com. Ex. 8 | 85.0%<br>42.8% |
| $CF_3$— | 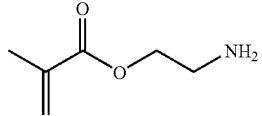 | Example 9<br>Com. Ex. 9 | 83.0%<br>40.5% |

As above, remarkable improvements were recognized in yield of the target product in Examples 3-9 in which water was made to be coexistent, as compared with Comparative Examples 3-9 of no water condition.

What is claimed is:

1. A process for producing a fluoroalkanesulfonamide derivative represented by the formula [3], $$R^2\text{—NH—SO}_2\text{—}R_f\text{—}R^1 \quad [3]$$

comprising reacting a fluoroalkanesulfonic anhydride represented by the formula [1], $$(R^1R_fSO_2)_2O \quad [1]$$

with an organic primary amine represented by the formula [2], $$R^2\text{—NH}_2 \quad [2]$$

in the presence of water and in the presence of a base selected from the group consisting of (a) a hydroxide of an alkali metal or alkaline-earth metal or (b) a basic salt containing an alkali metal or alkaline-earth metal, wherein $R_f$ represents a $C_1$-$C_{20}$ perfluoroalkylene group —$(C_aF_{2a})$— where a is an integer of 1-20, $R^1$ represents a fluorine atom, hydrogen atom, halo-substituted alkyl group, halo-substituted alkenyl group, or halo-substituted alkoxy group, $R_f$ and $R^1$ may be bonded together to form a cyclic structure, and $R^2$ represents an organic functional group containing at least one polymerizable double bond.

2. A process according to claim 1, wherein $R^1$ of the formula [1] represents a fluorine atom, and $R^2$ of the formula [2] represents a functional group represented by the formula [4], $$\text{A-O-}R^{2a}\text{—} \quad [4]$$

so that the fluoroalkanesulfonamide derivative is represented by the formula [3a],

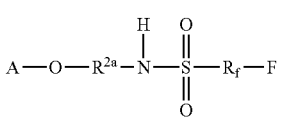

wherein A represents a functional group represented by the formula [4a], [4b] or [4c],

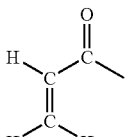

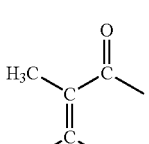

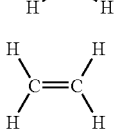

$R^{2a}$ represents an $C_1$-$C_{20}$ alkylene group, $C_5$-$C_{40}$ alicyclic group or $C_5$-$C_{40}$ aromatic group.

3. A process according to claim 1, wherein "$R^1R_f$" of the formula [1] represents a trifluoromethyl group, and $R^2$ of the formula [2] represents a functional group represented by the formula [5],

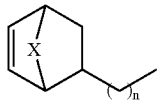

so that the fluoroalkanesulfonamide derivative is represented by the formula [3b],

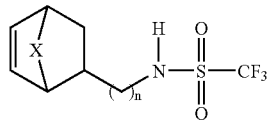

[3b]

wherein X represents —$CH_2$—, —O— or —S—, and n represents an integer of 0-6.

4. A process according to claim 3, wherein n represents an integer of 2-6 when X represents —$CH_2$—.

5. A process according to claim 1, wherein the reacting is conducted by intermittently or continuously adding the fluoroalkanesulfonic anhydride or water into a reaction system.

6. A process according to claim 1, wherein the reacting is conducted in the presence of a nonaqueous organic solvent that is at least one selected from the group consisting of pentane, hexane, heptane, benzene, toluene, xylene, mesitylene, diethylether, methyl-t-butyl ether, diisopropyl ether, tetrahydrofuran, methylene chloride, chloroform and carbon tetrachloride.

7. A process according to claim 1, wherein the base is at lease one selected from the group consisting of lithium hydroxide, sodium hydroxide, potassium hydroxide, magnesium hydroxide, calcium hydroxide, barium hydroxide, potassium carbonate, sodium carbonate, sodium hydrogencarbonate, sodium acetate, potassium acetate, disodium hydrogenphosphate, and dipotassium hydrogenphosphate.

8. A process according to claim 1, wherein the base is at lease one selected from the group consisting of sodium carbonate, potassium carbonate, sodium hydroxide, and potassium hydroxide.

9. A process according to claim 1, wherein the water is in an amount of 0.2-100 g per gram of the organic primary amine.

10. A process according to claim 6, wherein the nonaqueous organic solvent is in an amount of 0.5-100 g per gram of the organic primary amine.

11. A process according to claim 1, wherein the reacting is conducted at a temperature of −10° C. to 50° C.

12. A process for producing a fluoroalkanesulfonamide derivative represented by the formula [3], $R^2$—NH—$SO_2$—$R_f$—$R^1$  [3]

comprising the sequential steps of:
(a) charging a reactor with (i) an organic primary amine represented by the formula [2], $R^2$—$NH_2$  [2]

(ii) 0.2-100 g of water per gram of the organic primary amine, (iii) 0.5-100 g of a nonaqueous organic solvent per gram of the organic primary amine, and (iv) a base that is at least one selected from the group consisting of lithium hydroxide, sodium hydroxide, potassium hydroxide, magnesium hydroxide, calcium hydroxide, barium hydroxide, potassium carbonate, sodium carbonate, sodium hydrogencarbonate, sodium acetate, potassium acetate, disodium hydrogenphosphate, and dipotassium hydrogenphosphate; and
(b) intermittently or continuously introducing a fluoroalkanesulfonic anhydride represented by the formula [1], $(R^1R_fSO_2)_2O$  [1]

into the reactor at a temperature of −10° C. to 50° C., thereby reacting the fluoroalkanesulfonic anhydride with the organic primary amine,
wherein $R_f$ represents a $C_1$-$C_{20}$ perfluoroalkylene group —$(C_aF_{2a})$— where a is an integer of 1-20,
$R^1$ represents a fluorine atom, hydrogen atom, halo-substituted alkyl group, halo-substituted alkenyl group, or halo-substituted alkoxy group,
$R_f$ and $R^1$ may be bonded together to form a cyclic structure, and
$R^2$ represents an organic functional group containing at least one polymerizable double bond, and
wherein the nonaqueous solvent of step (a) is at least one selected from the group consisting of pentane, hexane, heptane benzene, toluene, xylene, mesitylene, diethyl ether, methyl-t-butyl ether, diisopropyl ether, tetrahydrofuran, methylene chloride, chloroform and carbon tetrachloride.

13. A process according to claim 12, wherein the base is at least one selected from the group consisting of sodium carbonate, potassium carbonate, sodium hydroxide, and potassium hydroxide,
wherein the water is in an amount of 2-6 g per gram of the organic primary amine, and
wherein the nonaqueous organic solvent is in an amount of 2-5 g per gram of the organic primary amine.

* * * * *